(12) United States Patent
Zwierstra et al.

(10) Patent No.: US 11,957,510 B2
(45) Date of Patent: Apr. 16, 2024

(54) PORTABLE HEADSET

(71) Applicant: Neurasignal, Inc., Los Angeles, CA (US)

(72) Inventors: Jan Zwierstra, Los Angeles, CA (US); Trevor Dunlop, Los Angeles, CA (US); Lane Stith, Los Angeles, CA (US)

(73) Assignee: Neurasignal, Inc., Los Angeles, CA (US)

( * ) Notice: Subject to any disclaimer, the term of this patent is extended or adjusted under 35 U.S.C. 154(b) by 0 days.

(21) Appl. No.: 17/900,076

(22) Filed: Aug. 31, 2022

(65) Prior Publication Data

US 2023/0063233 A1    Mar. 2, 2023

Related U.S. Application Data

(63) Continuation of application No. 16/112,612, filed on Aug. 24, 2018, now Pat. No. 11,471,126.

(Continued)

(51) Int. Cl.
| | |
|---|---|
| *A61B 8/00* | (2006.01) |
| *A61B 3/00* | (2006.01) |
| *A61B 5/00* | (2006.01) |
| *A61B 5/026* | (2006.01) |
| *A61B 5/06* | (2006.01) |

(Continued)

(52) U.S. Cl.
CPC .......... *A61B 8/4227* (2013.01); *A61B 3/0083* (2013.01); *A61B 5/026* (2013.01); *A61B 5/065* (2013.01); *A61B 5/6803* (2013.01); *A61B 6/0421* (2013.01); *A61B 6/501* (2013.01); *A61B 8/06* (2013.01); *A61B 8/0816* (2013.01); *A61B 8/40* (2013.01); *A61B 8/4209* (2013.01); *A61B 8/4218* (2013.01); *A61B 8/4427* (2013.01); *A61B 8/4461* (2013.01); *A61B 8/461* (2013.01); *A61B 8/488* (2013.01); *A61B 8/403* (2013.01); *A61B 2090/502* (2016.02); *A61B 2576/026* (2013.01); *A61F 9/008* (2013.01); *G06F 3/011* (2013.01)

(58) Field of Classification Search
CPC .... A61B 6/0421; A61B 8/4209; A61B 8/4461
See application file for complete search history.

(56) References Cited

U.S. PATENT DOCUMENTS

| | | |
|---|---|---|
| 4,499,593 A | 2/1985 | Antle |
| 6,275,564 B1 | 8/2001 | Ein-Gal |

(Continued)

FOREIGN PATENT DOCUMENTS

WO    WO-2014/060914 A1    4/2014

OTHER PUBLICATIONS

Final Office Action dated Apr. 9, 2021, from U.S. Appl. No. 16/112,612.

(Continued)

*Primary Examiner* — Jason M Ip
(74) *Attorney, Agent, or Firm* — Polygon IP, LLP

(57) ABSTRACT

Arrangements described herein relate to a headset. The headset includes a device. The device includes a transducer configured to interact with a head of a subject. The headset further includes a manually-operated registration system configured to delineate a workspace of the transducer at the head of the subject.

20 Claims, 19 Drawing Sheets

Related U.S. Application Data

(60) Provisional application No. 62/550,326, filed on Aug. 25, 2017.

(51) Int. Cl.

| | |
|---|---|
| *A61B 6/00* | (2006.01) |
| *A61B 6/04* | (2006.01) |
| *A61B 6/50* | (2024.01) |
| *A61B 8/06* | (2006.01) |
| *A61B 8/08* | (2006.01) |
| *A61B 90/50* | (2016.01) |
| *A61F 9/008* | (2006.01) |
| *G06F 3/01* | (2006.01) |

(56) References Cited

U.S. PATENT DOCUMENTS

| | | | |
|---|---|---|---|
| 6,577,888 B1* | 6/2003 | Chan | G01R 33/3415 |
| | | | 324/318 |
| 8,603,014 B2 | 12/2013 | Alleman et al. | |
| 9,668,768 B2* | 6/2017 | Piron | A61B 34/30 |
| 2003/0182713 A1 | 10/2003 | Rolla | |
| 2004/0016057 A1 | 1/2004 | Traut et al. | |
| 2004/0167530 A1* | 8/2004 | Hamel | A61B 17/66 |
| | | | 606/86 R |
| 2006/0225213 A1 | 10/2006 | Tomcany | |
| 2007/0270683 A1 | 11/2007 | Meloy | |
| 2010/0262008 A1 | 10/2010 | Roundhill | |
| 2011/0251489 A1 | 10/2011 | Zhang et al. | |
| 2012/0083682 A1 | 4/2012 | Klodell et al. | |
| 2013/0345718 A1 | 12/2013 | Crawford et al. | |
| 2015/0112153 A1 | 4/2015 | Nahum | |
| 2015/0297176 A1 | 10/2015 | Rincker et al. | |
| 2016/0030001 A1 | 2/2016 | Stein et al. | |
| 2017/0291037 A1 | 10/2017 | Tamiya et al. | |

OTHER PUBLICATIONS

Final Office Action dated May 16, 2019, from U.S. Appl. No. 16/112,612.
Final Office Action dated May 2, 2019, from U.S. Appl. No. 16/111,123.
International Search Report and Written Opinion dated Nov. 21, 2018, from application No. PCT/US2018/048014.
Non-Final Office Action dated Jun. 22, 2020, from U.S. Appl. No. 16/111,123.
Non-Final Office Action dated Jun. 22, from U.S. Appl. No. 16/112,612.
Non-Final Office Action dated Mar. 7, 2022, from U.S. Appl. No. 16/112,612.
Non-Final Office Action dated Nov. 16, 2018, from U.S. Appl. No. 16/111,123.
Non-Final Office Action dated Nov. 19, 2018, from U.S. Appl. No. 16/112,612.
Notice of Allowance dated Jun. 8, 2022, from U.S. Appl. No. 16/112,612.

* cited by examiner

PORTABLE HEADSET

CROSS-REFERENCE TO RELATED PATENT APPLICATIONS

This application is a continuation of U.S. application Ser. No. 16/112,612, filed Aug. 24, 2018, which claims priority from U.S. Provisional Application No. 62/550,326, filed on Aug. 25, 2017, the contents of each of which are incorporated herein by reference in their entireties.

BACKGROUND

For devices utilizing a headset whose performance is optimized by remaining stable with respect to a user's head (e.g., optical devices, surgical devices, scanning devices, medical diagnostic devices, automated Transcranial Doppler devices, and so on), alignment of the device with respect to particular areas of a patient's head during operation is important for accurate readings by the device. In addition, in certain scenarios, it is difficult to implement robust versions of a headset including a device for use on a subject (e.g., in emergency situations, in a military environment such as a war zone, in the field away from a hospital or ambulance, and so on). As such, it is desirable that a device attached to a headset remains fixed at an optimal position with respect to areas of a user's head during operation. It is also desirable that the headset including the device is portable and facilitates optimal use thereof for quick and easy implementation in the field.

SUMMARY

According to various arrangements, provided is a headset device that is portable and that allows for efficient and effective implementation by an administrator of the headset device.

According to various arrangements, there is provided a headset. The headset includes a device including a transducer configured to interact with a head of a subject. The headset further includes a manually-operated registration system configured to delineate a workspace of the transducer at the head of the subject.

In some arrangements, the headset further includes a housing encasing at least a portion of the device, wherein the registration system is located at the housing of the device.

In some arrangements, the registration system includes a registration window configured to be aligned with one or more anatomical features of the head of the subject.

In some arrangements, the registration window includes a transparent narrow slot penetrating through the housing such that the head of the subject is visible through the registration window.

In some arrangements, the registration window includes one or more indicators configured to be aligned with the one or more anatomical features of the head of the subject.

In some arrangements, the one or more indicators include a line spanning the length of the registration window.

In some arrangements, the registration system further includes one or more registration markers at the registration window, the one or more registration markers configured to be slidably positioned along the registration window to be aligned with corresponding one or more anatomical landmarks of the head of the subject.

In some arrangements, positions of the one or more registration markers in the registration window delineate one or more corresponding boundaries of the workspace of the transducer at the head of the subject.

In some arrangements, the one or more registration markers include a first registration marker at a first position along the registration window and a second registration marker at a second position along the registration window such that the first and second positions delineate the workspace of the transducer at the head of the subject.

In some arrangements, the first position is aligned with an eye of the subject and the second position is aligned with an ear of the subject.

In some arrangements, the device includes a linear encoder configured to convert positions of the registration window and the one or more registration markers into electrical signals to delineate the workspace of the transducer at the head of the subject.

In some arrangements, the headset further includes a track, wherein the housing is coupled to the track and configured to slide along the track with respect to the head of the subject.

In some arrangements, the track is located adjacent the head of the subject so that the housing is configured to slide along a side of the head of the subject.

In some arrangements, the housing is configured to slide along the track after the registration window is aligned with the one or more anatomical features of the head of the subject to position the transducer in the workspace at the head of the subject.

In some arrangements, the housing is configured to slide along the track for a predetermined distance.

In some arrangements, the predetermined distance is in a range from about 0.5 inches to about 2.5 inches.

In some arrangements, the headset further includes a tab, wherein responsive to actuation of the tab, the housing is configured to slide along the track.

In some arrangements, the headset further includes a tilt hinge, wherein the housing is configured to rotate about the tilt hinge with respect to the head of the subject.

In some arrangements, the tilt hinge is located adjacent the head of the subject so that the housing is configured to rotate along a side of the head of the subject.

In some arrangements, the headset further includes a tab, wherein responsive to actuation of the tab, the housing is configured to rotate about the tilt hinge.

In some arrangements, the headset further includes a body configured to receive the head of the subject.

In some arrangements, the device and the registration system are attached to the body.

In some arrangements, the device is located at an edge of the body and positioned to be adjacent a side of the received head of the subject.

In some arrangements, the device is connected to the registration system.

In some arrangements, the transducer is configured to collect data from the head of the subject.

In some arrangements, the data includes blood flow characteristics of the subject.

In some arrangements, the transducer is configured to transmit and receive ultrasound energy waves with respect to the head of the subject.

In some arrangements, the device further includes robotics configured to move the transducer with respect to the head of the subject.

In some arrangements, the registration system controls the robotics to restrain the transducer to within the workspace at the head of the subject.

According to various arrangements, there is provided a method of providing a headset. The method includes providing a device including a transducer configured to interact with a head of a subject. The method further includes providing a manually-operated registration system configured to delineate a workspace of the transducer at the head of the subject.

BRIEF DESCRIPTION OF THE FIGURES

Features and aspects of the present disclosure will become apparent from the following description and the accompanying example arrangements shown in the drawings, which are briefly described below.

DETAILED DESCRIPTION

The detailed description set forth below in connection with the appended drawings is intended as a description of various configurations and is not intended to represent the only configurations in which the concepts described herein may be practiced. The detailed description includes specific details for providing a thorough understanding of various concepts. However, it will be apparent to those skilled in the art that these concepts may be practiced without these specific details. In some instances, well-known structures and components are shown in block diagram form in order to avoid obscuring such concepts.

In the following description of various arrangements, reference is made to the accompanying drawings which form a part hereof and in which are shown, by way of illustration, specific arrangements in which the arrangements may be practiced. It is to be understood that other arrangements may be utilized, and structural changes may be made without departing from the scope of the various arrangements disclosed in the present disclosure.

Figure 1A:
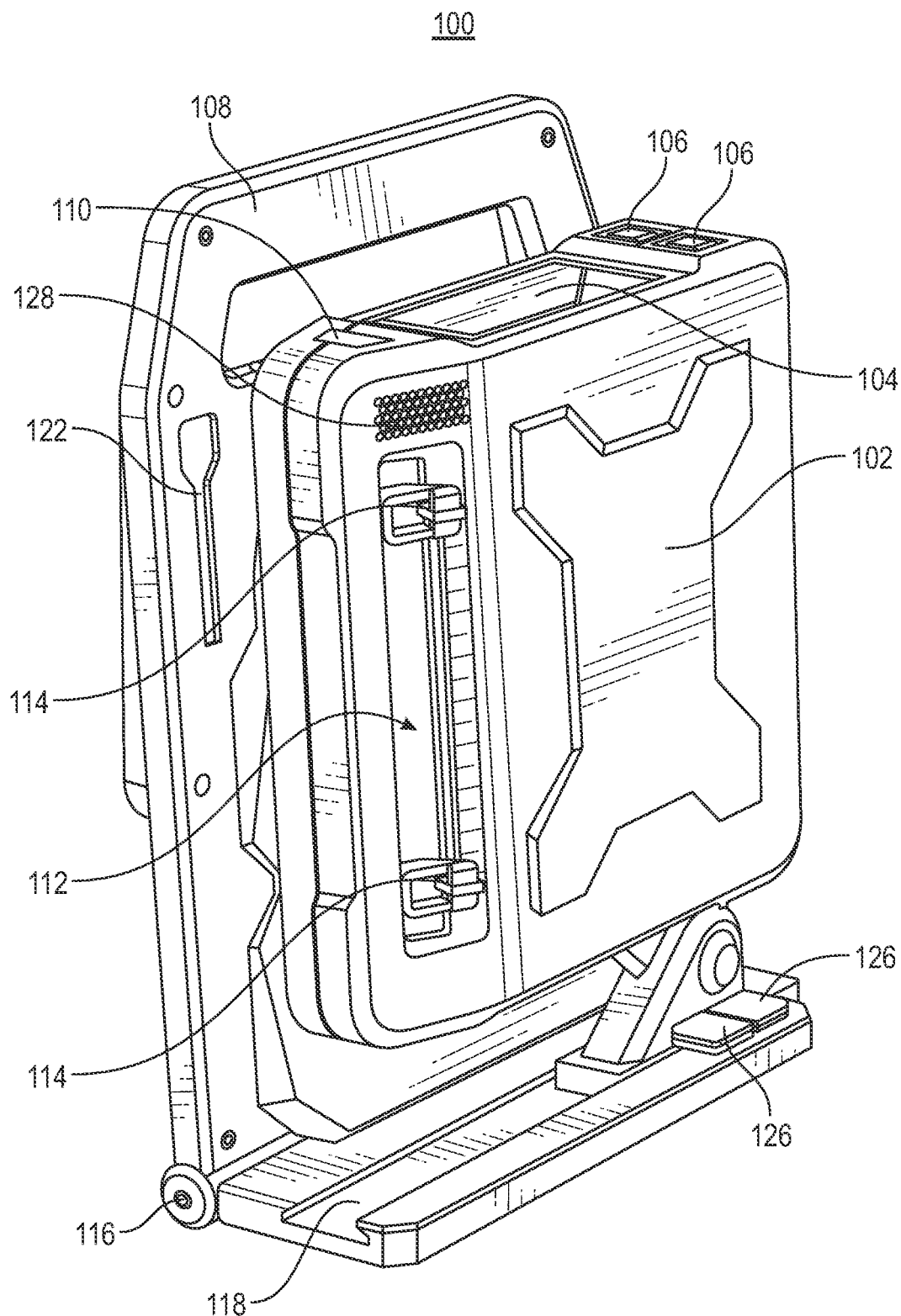
FIG. 1A, FIG. 1B, FIG. 1C, FIG. 1D, FIG. 1E, FIG. 1F, and FIG. 1G illustrate various views of a portable headset according to various arrangements.
Figure 1B:
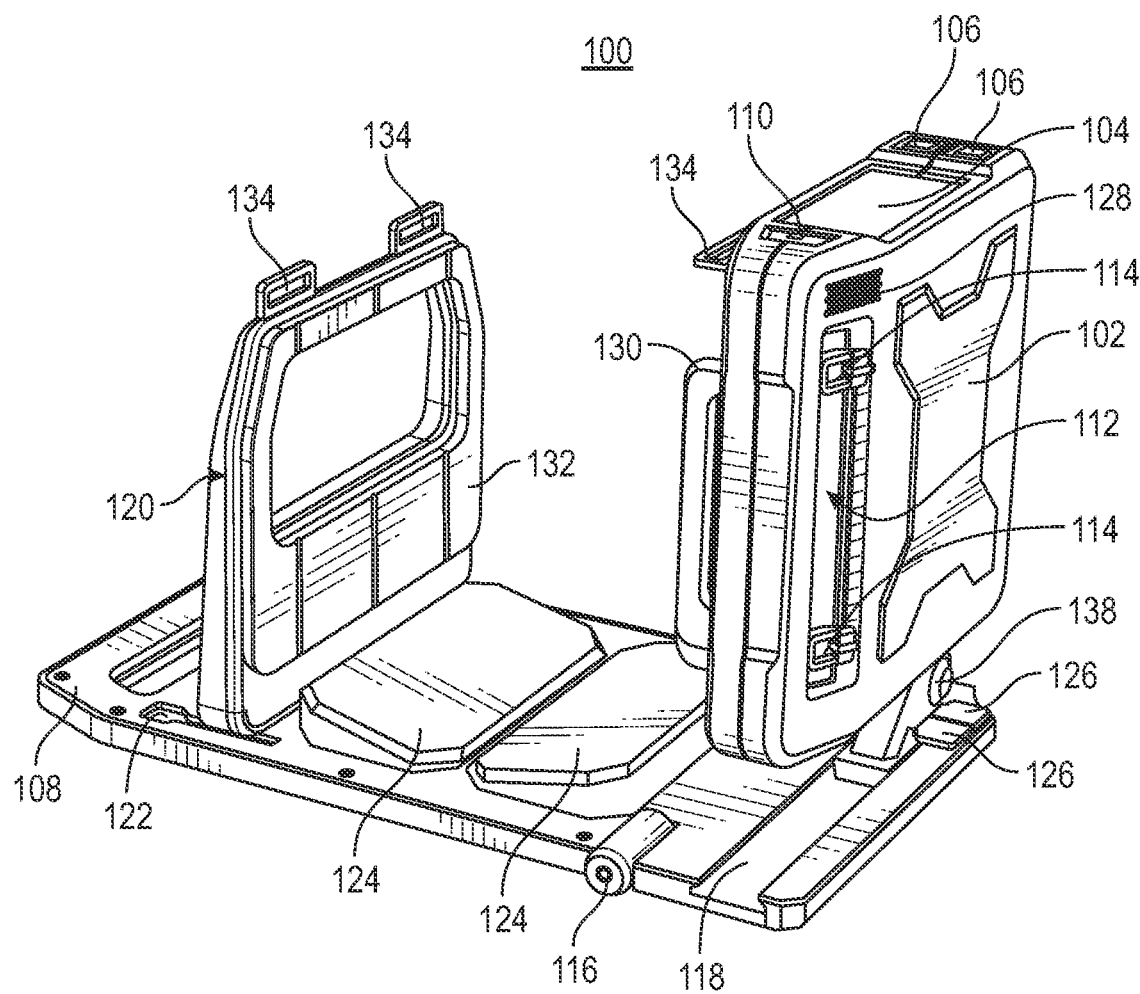
Figure 1C:
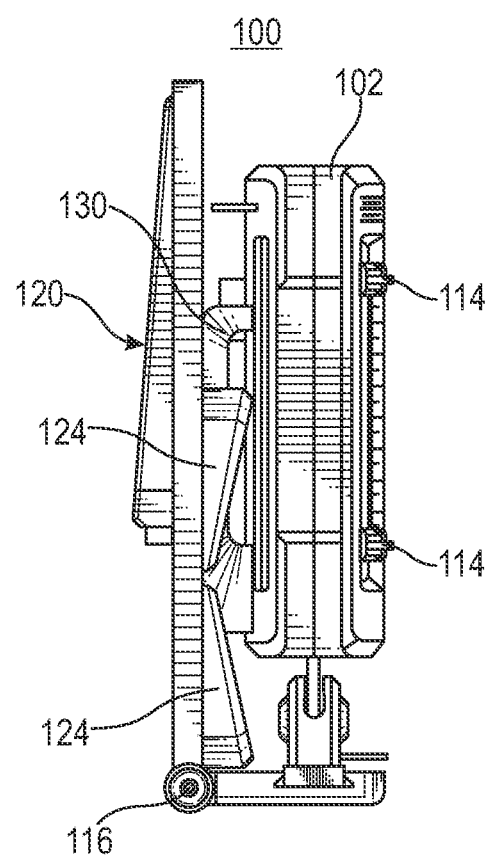
Figure 1D:
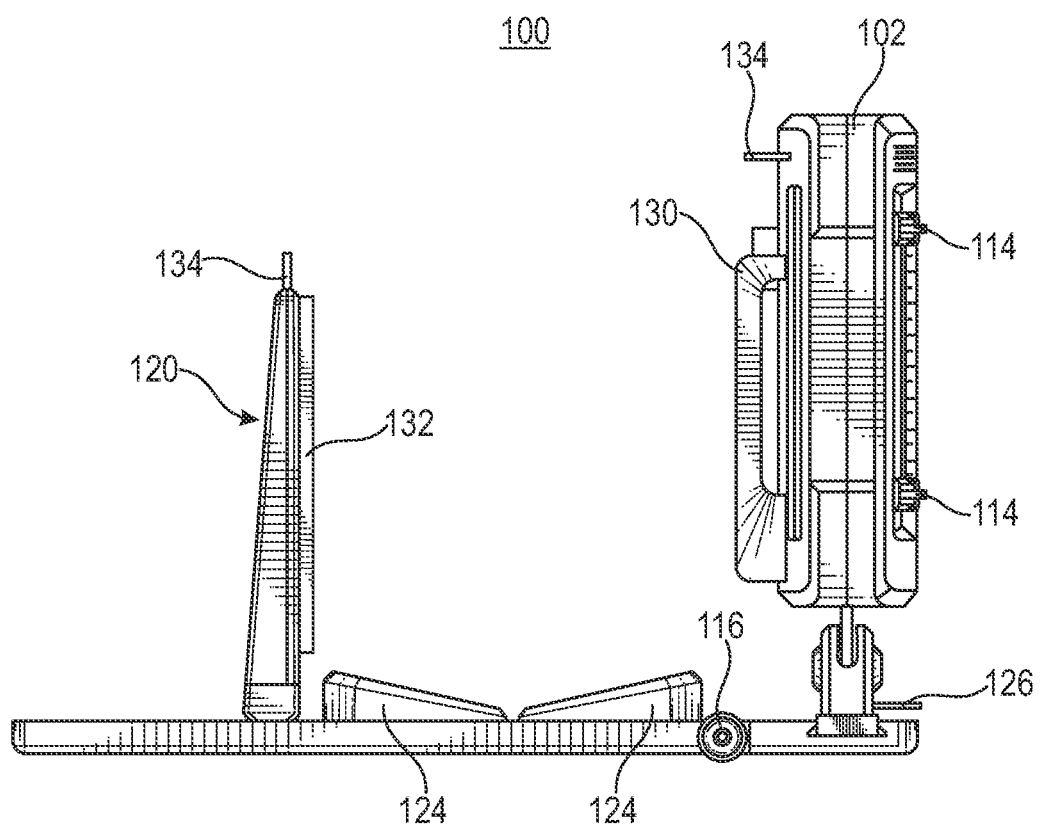
Figure 1E:
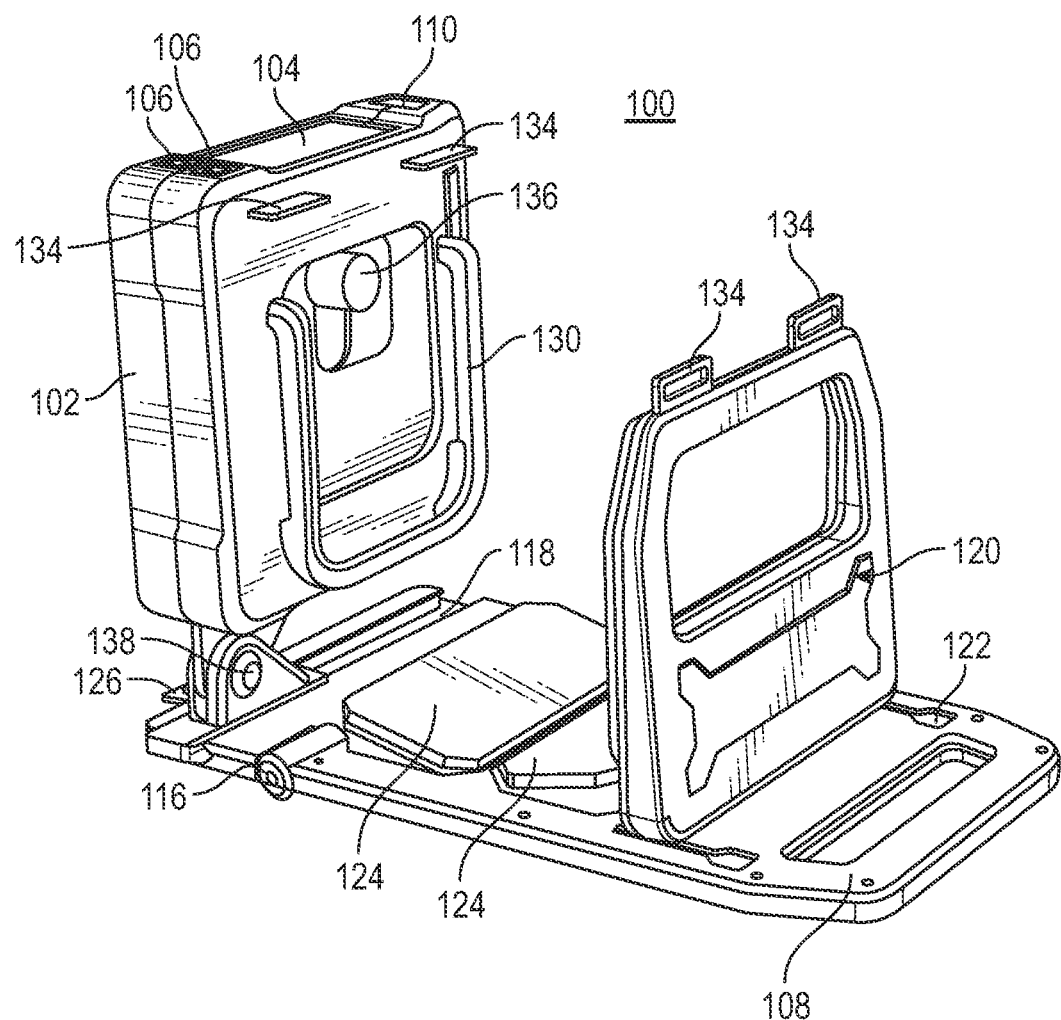
Figure 1F:
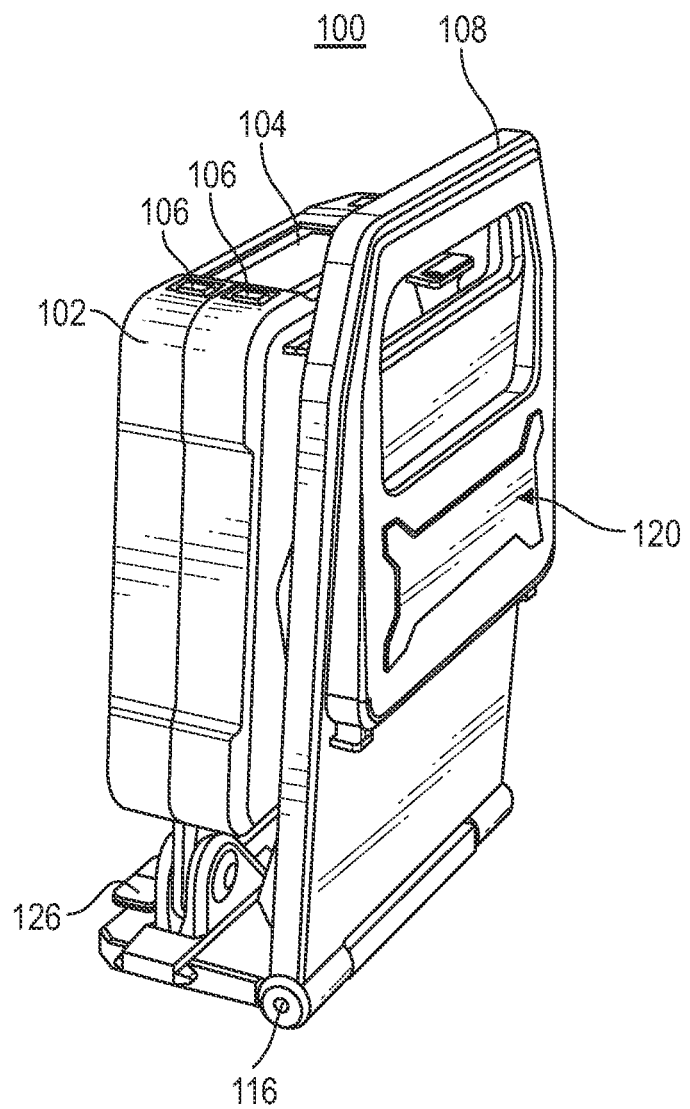
Figure 1G:
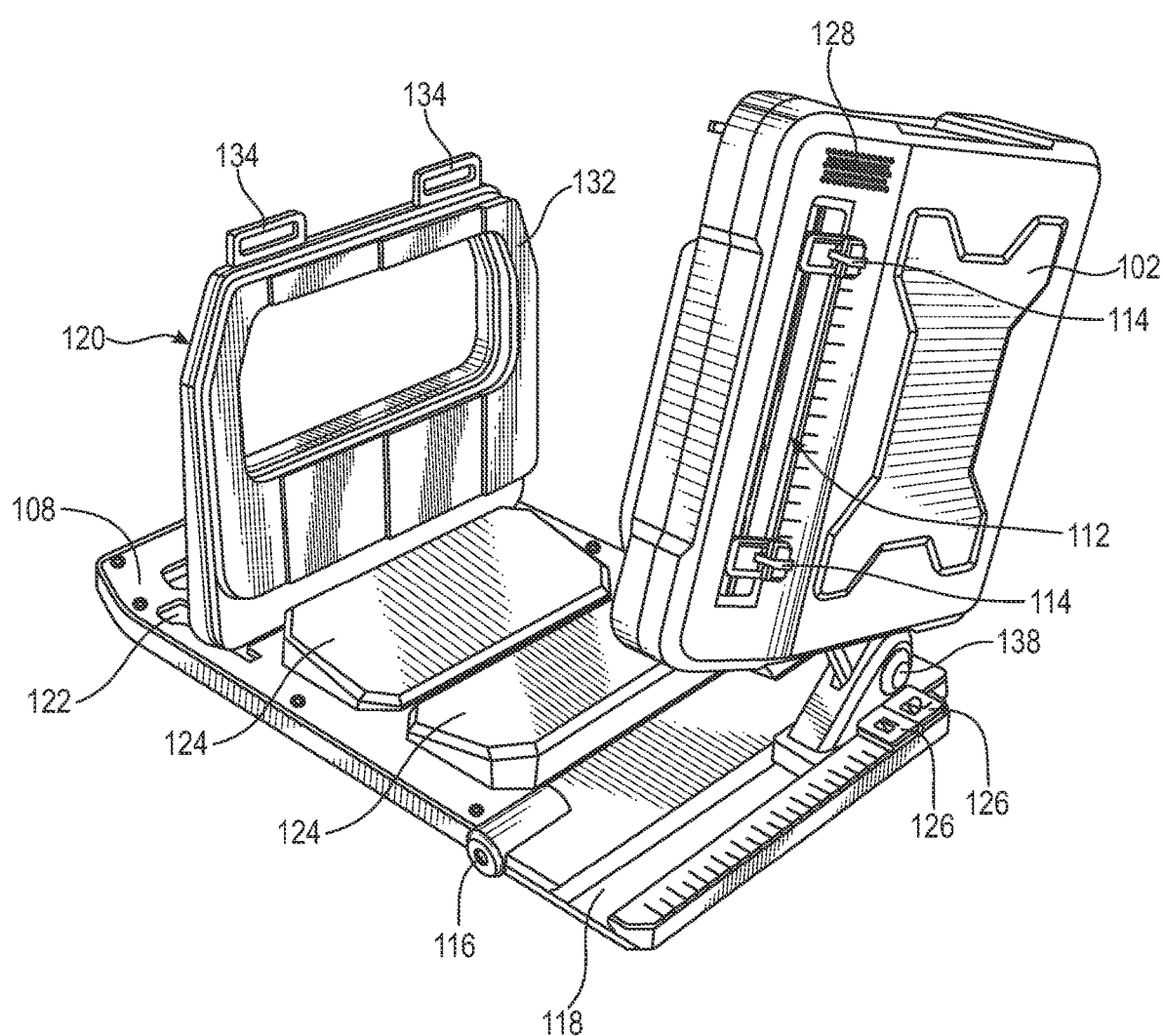

FIG. 1A, FIG. 1B, FIG. 1C, FIG. 1D, FIG. 1E, FIG. 1F, and FIG. 1G illustrate various views of a portable headset 100 according to various arrangements. In some arrangements, the portable headset 100 can be stored and carried in a folded (or compact or stored or stowed) state (e.g., as shown in FIGS. 1A, 1C, and 1F) and implemented in a deployed or open state (e.g., as shown in FIGS. 1B, 1D, 1E, and 1G).

In some arrangements, the portable headset 100 includes a device 102. In some arrangements, the device 102 is modular and can be attached and detached from the portable headset 100. In some arrangements, the device 102 is for use with respect to a head of a user (e.g., a subject, a patient, and the like). Examples of the device 102 include but are not limited to, an ocular monitoring system, a breathing device, a device for monitoring neurological activity, a surgical device, a device for monitoring radioactive traces, a Transcranial Doppler (TCD) device, or any other device suitable for use with the portable headset 100. In other arrangements, the device 102 includes a non-medical device for use with respect to a user's head.

In some arrangements, the device 102 includes a transducer or probe 136 and robotics for controlling the probe 136. The probe 136 is configured to collect data (e.g., physiological data, biometric data, imaging data, and the like) of a subject. For example, the robotics are configured to translate the probe 136 along a surface of a head and move the probe 136 towards and away from the head. In some arrangements, an end of the probe 136 interfaces with the robotics, and the robotics include components, such as, but not limited to, a motor assembly, electronics, and the like for controlling the probe 136 (e.g., control z-axis pressure, normal alignment, or the like of the probe 136). In that regard, the robotics are configured to align the probe 136 with respect to the head. In some arrangements, the robotics are housed within a housing of the device 102, while the probe 136 is exposed from the housing to be able to interact with a head of a subject.

In other words, the robotics are configured to translate the probe 136 along a surface of the head and to move the probe 136 with respect to (e.g., toward and away from) the head along various axes in the Cartesian, spherical, and rotational coordinate systems. For example, the robotics can include a multiple degree-of-freedom (DOF) TCD transducer positioning system with motion planning. In some arrangements, the robotics are capable of supporting two, three, four, five, or six DOF movements of the probe 136 with respect to the head. In some instances, the robotics can translate in X and Y axes (e.g., along a surface of the head) to locate a temporal window region, and in Z-axis with both force and position feedback control to both position and maintain the appropriate force against the skull/skin to maximize signal quality by maintaining appropriate contact force. Two angular DOF (e.g., pan and tilt) may be used to maximize normal insonation of blood vessels to maximize velocity signals.

In some arrangements, an end of the probe 136 is operatively coupled to or otherwise interfaces with the robotics. The robotics include components, such as but not limited to a motor assembly and the like for controlling the positioning of the probe 136 (e.g., controlling Z-axis pressure, controlling a position on a plane defined by the X-axis and the Y-axis, normal alignment, or the like of the probe 136). In some arrangements, the registration of the probe 136 against the head is accomplished using the robotics to properly position and align the probe 136 in the manner described.

In some arrangements, the probe 136 includes a first end and a second end that is opposite to the first end. In some arrangements, the first end includes a concave surface that is configured to be adjacent to or contact a scanning surface (e.g., a head of a subject). The concave surface is configured with a particular pitch to focus generated energy towards the scanning surface. In some arrangements, the device 102 is a TCD apparatus such that the first end of the probe 136 is configured to be adjacent to or contact and align along a human head (e.g., a side of the human head), and the first end of the probe 136 is configured to provide ultrasound wave emissions from the first end and directed into the human head (e.g., towards the brain). In other arrangements, the probe 136 is configured to emit other types of waves during operation, such as, but not limited to, infrared, x-rays, or the like.

In some arrangements, the second end of the probe 136 is coupled to the robotics. In some arrangements, the second end of the probe 136 includes a threaded section along a portion of the body of the probe 136, and the second end is configured to be secured at the robotics via the threads (e.g., by being screwed into the robotics). In other arrangements, the probe 136 is secured at the robotics by any other suitable connecting means, such as, but not limited to, welding, adhesive, one or more hooks and latches, one or more separate screws, press fittings, or the like.

In other arrangements, the probe 136 is attached within the portable headset 100 without any robotics, such that the probe 136 is configured to be manually operated by an operator while the portable headset 100 is positioned on a user's head. For example, a user's head can be placed in the portable headset 100 and an operator can manually shift and orient the probe 136 while the probe 136 is activated.

Similar and further disclosure regarding probe systems that can be used in conjunction with the headsets described herein can be found in non-provisional patent application Ser. No. 15/399,648, titled ROBOTIC SYSTEMS FOR CONTROL OF AN ULTRASONIC PROBE, and filed on Jan. 5, 2017, which is incorporated herein by reference in its entirety.

In some arrangements, the device 102 includes other medical and non-medical devices that are used and stabilized with respect to a user's head. For example, in some arrangements, the device 102 includes an ocular device that is optimized by maintaining positioning and alignment with a user's eyes (e.g., if the ocular device is shifted with respect to a user's eyes, performance of the ocular device may decline). In some arrangements, the ocular device is attached at the portable headset 100 so as to cover the eyes of a patient. As an example of a non-medical device use with respect to the portable headset 100, in some arrangements, the portable headset 100 can be used in connection with the ocular device that is a virtual reality device configured to provide a virtual experience to the user such that any disturbance of the positioning of the ocular device in front of the user's eyes may cause a degradation in the user's virtual experience.

In some arrangements, the ocular device is a medical device designed to track ocular behavior of a subject (e.g., to diagnose whether the user has experienced a concussion). In other arrangements, the ocular device is an ocular diagnosis or treatment tool for determining or adjusting vision of the user. As an example, the ocular device is a device for correcting imperfect vision of a user (e.g., laser eye surgery). As another example, in some arrangements, the ocular device is an ocular diagnostic tool for determining a vision prescription of a user, presence of one or more eye conditions (e.g., glaucoma, cataracts, ocular hypertension, uveitis, or the like), and so on. In some arrangements, the ocular device is designed to cover and interact with both eyes simultaneously or in sequence. In other arrangements, the ocular device is designed to cover and interact with a single eye (e.g., while the other eye remains uncovered). The ocular device can be provided with any of the headset apparatuses described herein.

In some arrangements, the device 102 includes a display 104 (e.g., an electronic display). In some arrangements, the display 104 is configured to provide instructions for operation of the device 102, requests inputs into the device 102, displays results of operation of the device 102, and so on. In some arrangements, the display 104 is a touchscreen configured to accept inputs when a user interacts with the display 104. The device 102 further includes one or more inputs 106 (e.g., user interactive elements). The inputs 106 include buttons that allow a user to control the device 102. In some arrangements, the inputs 106 trigger one or more operations of the device 102, such as, but not limited to, start operation, cancel operation, and the like. In some arrangements, the device 102 further includes a power input 110 (e.g., a button) configured to toggle the device 102 on and off. In some arrangements, the device 102 further includes a speaker 128 configured to emit audio from the device 102, such as, but not limited to, audible instructions, requests, alerts, notices, and the like. In some arrangements, the speaker 128 is configured to receive audio commands from a user for controlling operation of the device 102 (e.g., initiate operation, cancel operation, power on/off, and so on).

In some arrangements, the device 102 further includes a registration window 112 and registration markers 114. The housing of the device 102 structurally supports the registration window 112 in some examples. In some arrangements, the registration window 112 is or includes a transparent narrow slot that penetrates through the device 102 or the housing for the device 102, for allowing an operator to see through the device 102 or the housing. In some arrangements, the registration window 112 is an empty space in the housing of the device 102. In other arrangements, the registration window 112 includes a transparent material within the empty space, such as, but not limited to, plastic (e.g., Plexiglas), glass, and the like. In particular arrangements, the registration window 112 includes an indicator (e.g., a line spanning the length of the registration window 112) for allowing an operator to correctly align the registration window with appropriate facial features of the subject. The registration markers 114 are structurally (e.g., slidably) supported by the housing of the device 102 and the registration window 112. In some arrangements, the registration markers 114 are configured to slide along the registration window 112 by an operator and be positioned at certain locations along the registration window 112. In some arrangements, the space between the registration markers 114 dictates, corresponds to, or otherwise indicates the scanning space of the device 102. The scanning space is defined as the boundaries of a workspace of the probe 136, e.g., where the probe 136 can travel during operation of the device 102 during its operation. Further details regarding this mechanical registration of the device 102 using the registration window 112 and the registration markers 114 are disclosed below.

In some arrangements, the device 102 further includes one or more tabs 126. The tabs 126 are configured to allow movement of the device 102 (e.g., the movement of the housing of the device 102) when one of the tabs 126 is pressed. For example, upon actuation of a first one of the tabs 126, the device 102 is free to slide forward and backward along a track 118 of the portable headset 100. As another example, upon actuation of a second one of the tabs 126, the device 102 and the housing of the device 102 are free to rotate upward and downward about a tilt hinge 138 of the portable headset 100. In some arrangements, the device 102 is free to be moved as long as one of the tabs 126 is depressed such that the device 102 is locked into place after the depressed tab 126 is released. In other arrangements, the device 102 is free to be moved after a first press or actuation of one of the tabs 126 and is locked in place after a second press or actuation of the same tab 126.

In some arrangements, the device 102 has a guard 130 attached thereto. The guard 130 is proximate and surrounds an area of the device 102 that includes the probe 136. Accordingly, the guard 130 is configured to protect the device 102 (e.g., the probe 136) from damage while the portable headset 100 is in the folded state by blocking the rest of the portable headset 100 from contacting the inner surface of the device 102 (e.g., the probe 136). For example, when the portable headset 100 is in the folded state, the guard 130 allows for a space or void between the two segments of the portable headset 100 that are folded against each other. In some arrangements, the guard 130 is made from any suitable material for protecting the device 102 from other components of the portable headset 100, such as, but not limited to, plastic, rubber, metal, foam, and the like. In some arrangements, the guard 130 includes a protective sleeve along a length of the guard 130, and the protective sleeve can be made from any suitable soft material (e.g., for providing a cushioning), such as, but not limited to, closed cell foam, open cell foam, self-skinning open or closed cell foams, cast, aerated, or extruded silicone or urethane, polyurethane gels that are configured to distribute pressure efficiently, or the like.

In some arrangements, the portable headset 100 includes one or more cushions 124 configured to receive a subject's head. In some arrangements, the cushions 124 are made from any suitable soft material, such as, but not limited to, closed cell foam, open cell foam, self-skinning open or closed cell foams, cast, aerated, or extruded silicone or urethane, polyurethane gels that are configured to distribute pressure efficiently, or the like. In some arrangements, the cushions 124 have any suitable firmness for supporting a head, such as, but not limited to, in a range of about 0.1 pound per square inch (psi) to about 60 psi (e.g., in a range of about 0.1 psi to about 10 psi) or within other suitable ranges of firmness. In some arrangements, the cushions 124 have memory for expanding to fit contours of a head. In some arrangements, the cushions 124 compress and expand after a user's head is placed in the portable headset 100. In some arrangements, the cushions 124 are manufactured by any suitable process for affixing the cushions 124 within the portable headset 100, such as, but not limited to, injection molding, laminating, adhesive mounting (e.g., gluing or bonding), co-molding, co-casting, injection, snapping, by Velcro fastening, by hook and loop fastening, friction fitting, attaching with barbs, using screw bosses, or the like.

In other arrangements, the cushions 124 include an inflatable bladder. In some arrangements, the bladder is a hollow void that is filled manually or with a pump. In such arrangements, the inflatable bladder is self-inflating with an internal structure that has a memory and that expands within the bladder to inflate to at least 90% capacity. In further arrangements, inflation is assisted with an integrated pump or an external filling or pumping source. In some arrangements, the inflatable bladder is filled with air, gas, liquid, or any other suitable element for receiving a user's head. In other arrangements, the bladder is filled with plastic beads or pellets. In particular arrangements, the bladder that is filled with plastic beads or pellets becomes rigid, so as to capture a patient's head, when a vacuum is applied to the bladder.

In some arrangements, the cushions 124 are shaped as wedges that are tapered towards each other such that a head of a subject is funneled or captured between the cushions 124, to maintain a position of the head of the subject. Accordingly, a subject's head is directed towards and maintained in the middle of the portable headset 100 at a central location between the cushions 124 such that the head is held physically stable for scanning operations to be performed by the device 102. In some arrangements, the cushions 124 provide a dual purpose, in addition to receiving and holding a subject's head when the portable headset 100 is in the deployed state, the cushions 124 also provide extra cushioning and protection for the device 102 (e.g., the inner surface of the device 102 including the probe 136) when the portable headset 100 is in a folded or stored state. For example, the cushions 124 contact and press against the inner surface of the device 102 (e.g., an inner surface of the housing supporting the device 102) when the portable headset 100 is in the folded state. In some arrangements, the cushions 124 are shaped narrowly enough so as to fit within a width of the guard 130 when the portable headset 100 is in the folded state. In further arrangements, the cushions 124 are shaped so that the central portion of the cushions 124 (e.g., the portion that has the narrowest thickness or where the two separate cushions 124 face each other) overlaps the bottom segment of the guard 130 so that the guard 130 does not contact the cushions 124 and so that the portable headset 100 can fold compactly.

In some arrangements, the portable headset 100 is converted from the folded state to the deployed state, and vice versa, by folding and unfolding a body of the portable headset 100 about a pivot hinge 116. The body of the portable headset 100 includes a first portion having the track 118. The first portion is operatively coupled to the device 102 and the housing thereof, and structurally supports the device 102 and the housing in an upright position (e.g., 90° with respect to the first portion). The headset 100 is configured to be in a folded state when the first portion and the second portion are folded toward each other. The headset 100 is configured to be in a deployed state when the first portion and the second portion are unfolded away from each other. The body of the portable headset 100 includes a second portion supporting the one or more cushions 124 and the head restraint 120. Thus, the second portion is configured to at least support the head of the subject when the portable headset 100 is in the deployed state. The second portion structurally supports the head restraint 120 in an upright position (e.g., 90° with respect to the second portion) when the portable headset 100 is in the deployed state, in the manner described. The second portion having grooves 122. A handle 108 extends from the second portion and is coplanar with the second portion. The first portion and the second portion are pivotally connected via the pivot hinge 116. The first portion and the second portion are coplanar when the portable headset 100 is in the deployed state, such that the first portion and the second portion can be placed on any surface that is flat or substantially flat. The first portion and the second portion are at 90° with respect to each other when the portable headset 100 is in the folded state, to conserve space. While in the folded state, the portable headset 100 includes the handle 108 for easily grabbing and carrying of the portable headset 100 (e.g., the handle 108 is beneficial in emergency situations that call for quick access to the portable headset 100). In addition, the portable headset 100 in the folded state includes the head restraint 120. In some arrangements, the head restraint 120 is attached to an outside surface of the portable headset 100 for storage, and the head restraint 120 is attached to the portable headset 100 by any suitable attachment mechanism, such as, but not limited to, snap-fitting, adhesive, and the like. While in the folded state, an opening of the head restraint 120 aligns with an opening of the handle 108 to provide an area through which a user can grab and hold on to the portable headset 100 via the handle 108.

In some arrangements, the head restraint 120 is detachable from the outer surface of the body the portable headset 100 and attachable to an inner surface of the body of the portable headset 100 when in the deployed state. For example, to install the head restraint 120 to the body when the portable headset 100 is in the deployed state, a bottom of the head restraint 120 (e.g., protrusions extending from the bottom of the head restraint 120) can fit into a plurality of grooves 122 located at opposite sides of the inner surface of the portable headset 100. Furthermore, a location of the head restraint 120 with respect to the cushions 124, as well as the distance between the head restraint 120 and the device 102, are adjustable by sliding the head restraint 120 along a length of the grooves 122. Accordingly, various head sizes and shapes can be accommodated and stabilized by adjusting the position of the head restraint 120 by sliding the head restraint 120 against a subject's head when the head is placed on top of the cushions 124.

In some arrangements, the head restraint 120 includes padding 132 for providing a soft and comfortable surface for contacting a subject's head. In some arrangements, the padding 132 is made from any suitable soft material, such as, but not limited to, closed cell foam, open cell foam, self-skinning open or closed cell foams, cast, aerated, or extruded silicone or urethane, polyurethane gels that are configured to distribute pressure efficiently, or the like. In some arrangements, the head restraint 120 includes one or more strap loops 134 for anchoring a strap for providing further restraint of a subject's head within the portable headset 100. In further arrangements, one or more additional strap loops 134, corresponding to the strap loops 134 located at the head restraint 120, are located at the inner surface of the device 102. Accordingly, one or more straps can be tied between the strap loops 134 to stabilize and restrain a subject's head, as shown and described below.

In other arrangements, the head restraint 120 is attached to and lays flat against an inner surface of the portable headset 100 such that the head restraint 120 is enclosed within the portable headset 100 when in the folded state. In particular arrangements, the head restraint 120 unfolds upward when the portable headset 100 is in the unfolded state to position the head restraint 120 upright so that the padding 132 can contact a subject's head. In such arrangements, the head restraint 120 is configured to fold downward when the portable headset 100 is to be switched into the folded state.

In some arrangements, the body of the portable headset 100 is made from any suitable durable material, such as, but not limited to, hard plastic, metals, aluminum, steel, titanium, magnesium, various alloys, rigid plastics, composites, carbon fiber, fiber glass, expanded foam, compression molded foam, stereolithography (SLA) or Fused Deposition Modeling (FDM)-made materials, Reaction Injection Molding (RIM) molding, acrylonitrile butadiene styrene (ABS), thermoplastic olefin (TPO), nylon, polyvinyl chloride (PVC), fiber reinforced resins, a composite thereof, an alloy thereof (e.g., a cast alloy), or the like.

In some arrangements, the portable headset 100 is configured to scan either side of a subject's head. For example, the subject's head can be introduced into the portable headset 100 from either side of the portable headset 100 such that the device 102 is capable of operation at either side of the subject's head, depending on from which direction the head is placed into the device 102. In other words, in some arrangements, the portable headset 100 is designed so that it can be rotated 180-degrees to enable measurements on both sides. In some arrangements, the portable headset 100 is designed such that a second automated device 102 can be attached at an opposite end of the portable headset 100 for faster bilateral scans. Accordingly, in some arrangements, the portable headset 100 is configured for bilateral application with respect to a subject's head. As such, if only one particular side of a subject's head is suitable for scanning by the device 102 (e.g., in a situation where the opposite side of the subject's head is injured), then the portable headset 100 is configured to accommodate such a subject's head. In further arrangements, both sides of a subject's head can be scanned for more thorough results.

In some arrangements, the portable headset 100 includes a portable power supply for supplying power to the device 102. For example, in some arrangements, the power supply includes a rechargeable battery (e.g., a 54.5-watt-hour lithium-polymer battery). In some arrangements, the power supply holds enough charge to power the device 102 for a substantial amount of time (e.g., about 100 or more hours of monitoring or about 5 or more hours of continuous scanning), and is lightweight enough to allow the portable headset 100 to be carried easily by an operator (e.g., the portable headset 100 can weigh less than about 5 pounds).

FIG. 2A, FIG. 2B, FIG. 2C, and FIG. 2D illustrate various views of the portable headset 100 shown in FIGS. 1A-1G with a human head 200 positioned therein according to various arrangements.

Figure 2A:
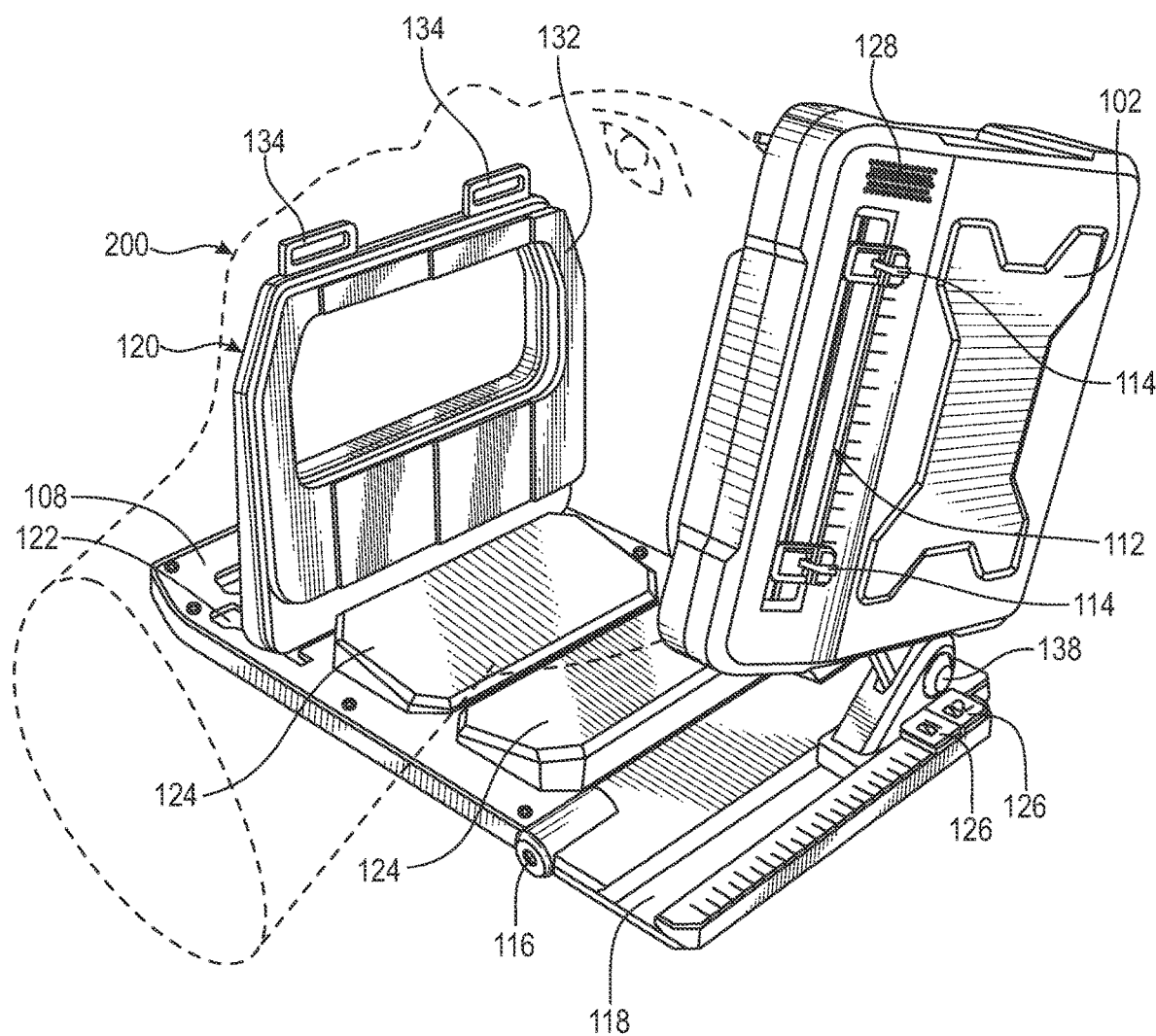
FIG. 2A, FIG. 2B, FIG. 2C, and FIG. 2D illustrate various views of the portable headset shown in FIGS. 1A-1G with a human head positioned therein according to various arrangements.
Figure 2B:
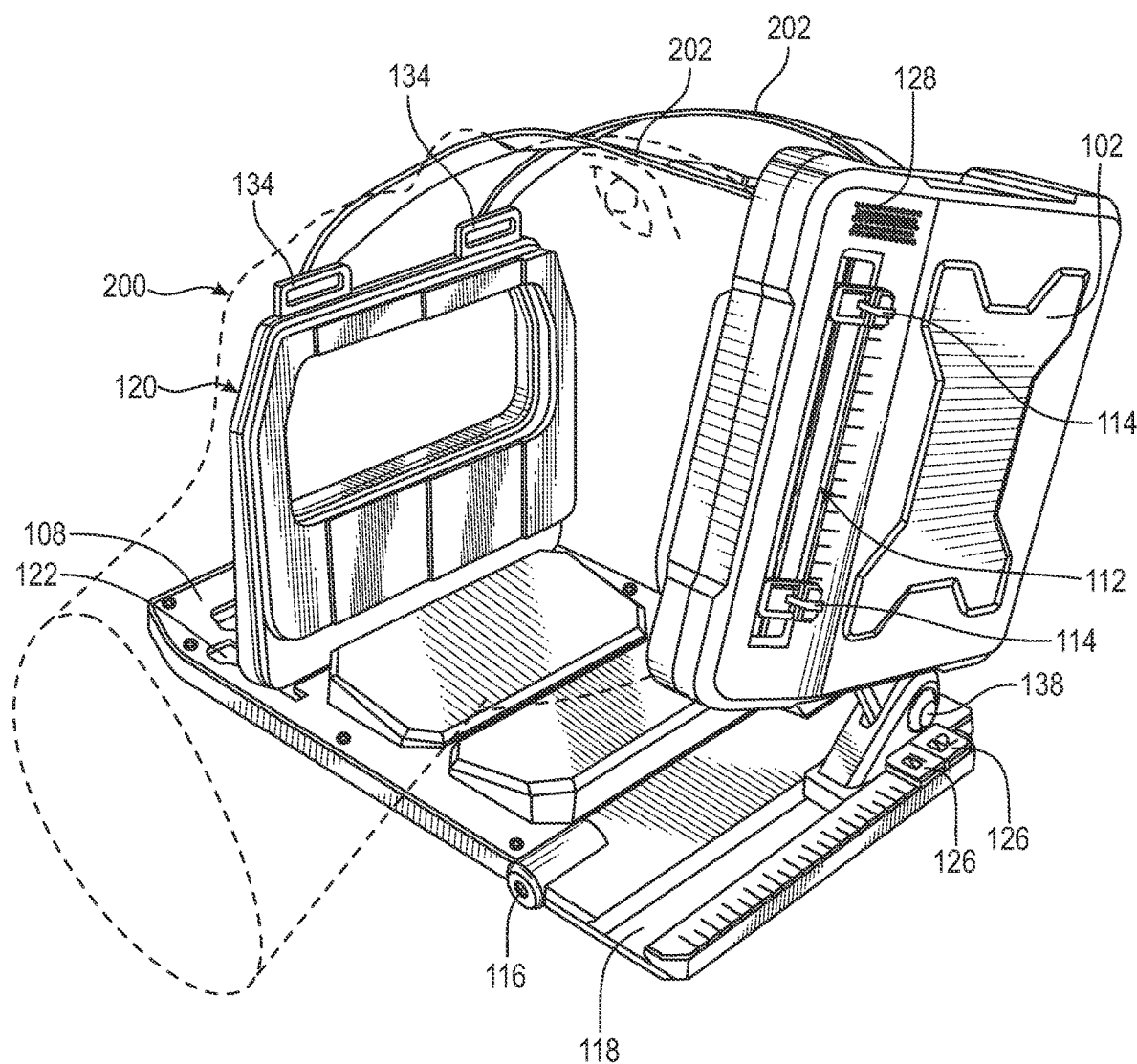
Figure 2C:
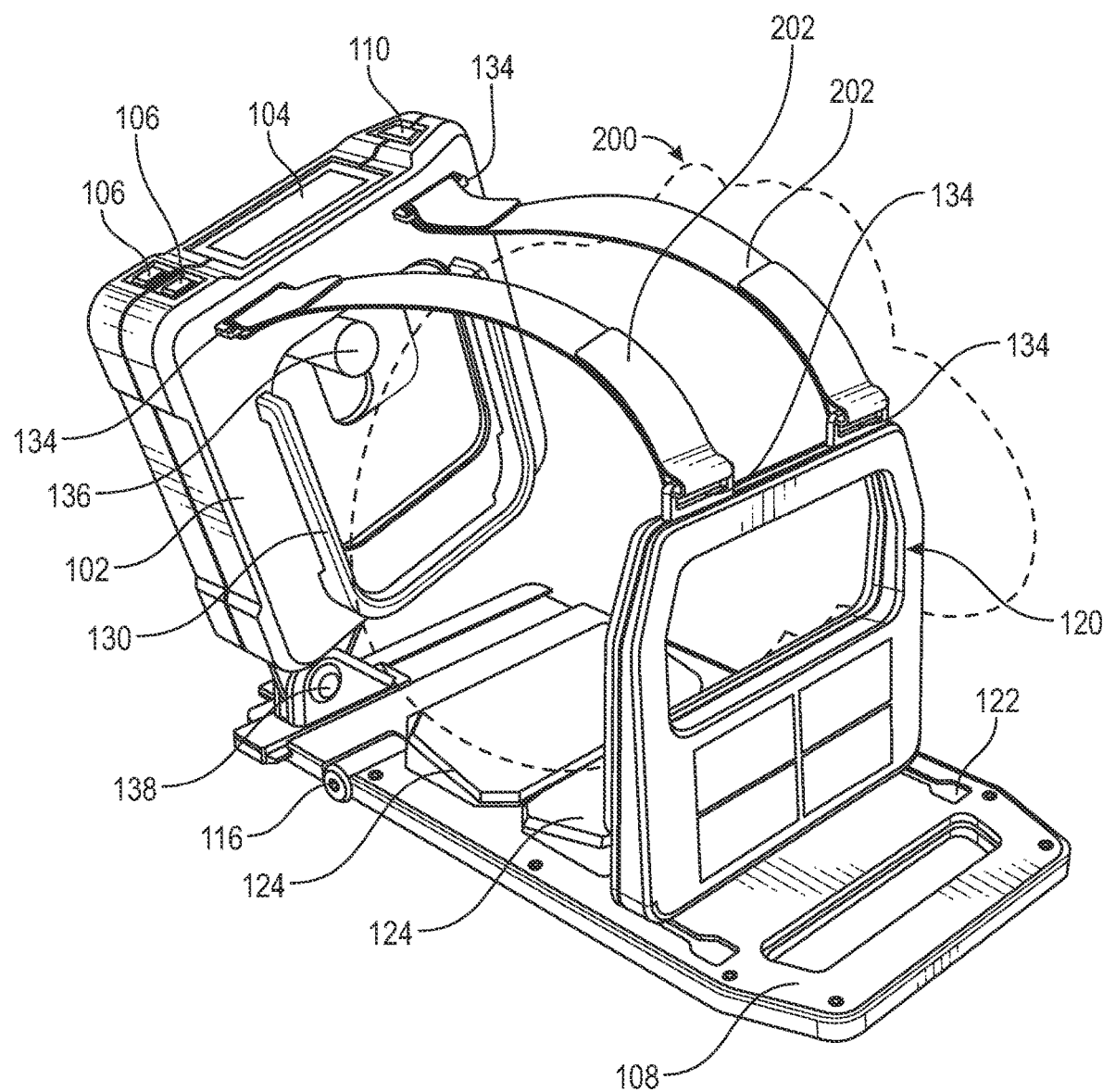
Figure 2D:
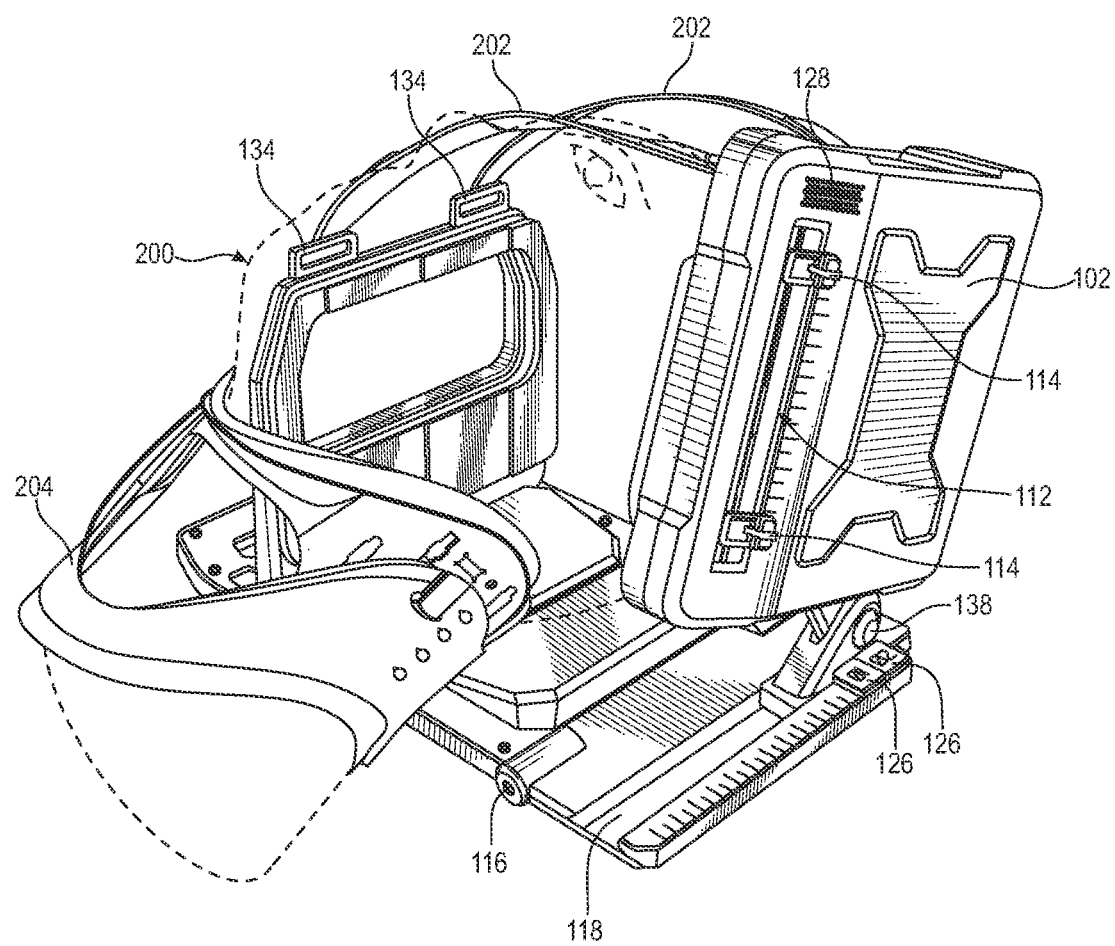

In some arrangements, the subject's head 200 is positioned such that a back of the head 200 rests on the cushions 124 so that the head 200 is facing upwards. The device 102 and the housing thereof is located at a first side of the head 200 and the head restraint 120 is located at a second side of the head 200 opposite to the first side of the head 200 when the portable headset 100 is in the deployed state. The head restraint 120 and the device 102 face each other when the portable headset 100 is in the deployed state. In some arrangements, one or more straps 202 are positioned across a forehead of the head 200 to provide further stabilization and restraint of the head 200. In some arrangements, the straps 202 contact and are held tight against the forehead so as to impart a downward force against the head 200 towards the cushions 124. In further arrangements, both ends of each of the straps 202 are anchored or tied at the respective strap loops 134 located at the head restraint 120 and the device 102. In some arrangements, the one or more straps 202 are made from any suitable material for restraining the head 200 while also being comfortable for the subject, such as, but not limited to, nylon, cloth, and the like. In some arrangements, the portable headset 100 is capable of operating on subjects that are wearing a cervical collar (or cervical brace) 204 (e.g., as shown in FIG. 2D).

FIG. 3A, FIG. 3B, FIG. 3C, FIG. 3D, FIG. 3E, and FIG. 3F illustrate stages of operation of the portable headset 100 shown in FIGS. 1A-1G according to various arrangements.

Figure 3A:
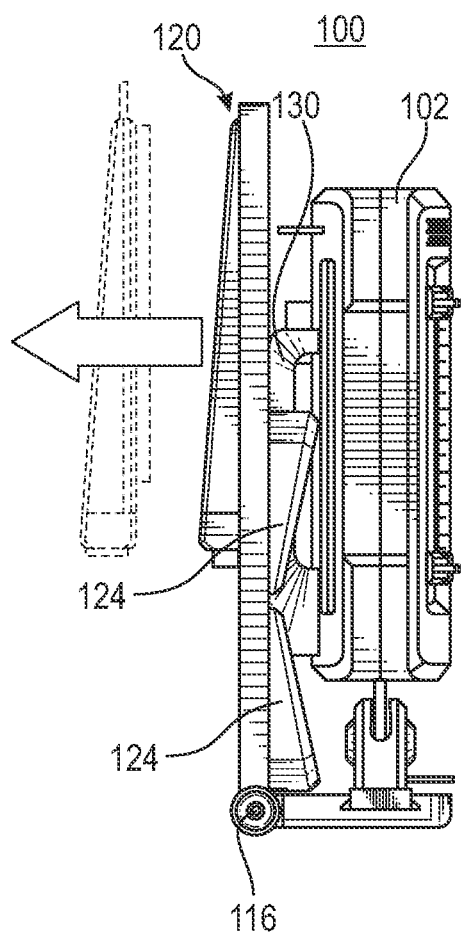
FIG. 3A, FIG. 3B, FIG. 3C, FIG. 3D, FIG. 3E, and FIG. 3F illustrate stages of operation of the portable headset shown in FIGS. 1A-1G according to various arrangements.

Referring to FIG. 3A, in some arrangements, the portable headset 100 is in the folded or stored state. The head restraint 120 is first detached from the outer surface of the portable headset 100. For example, the head restraint 120 can be simply pulled off of the portable headset 100.

Figure 3B:
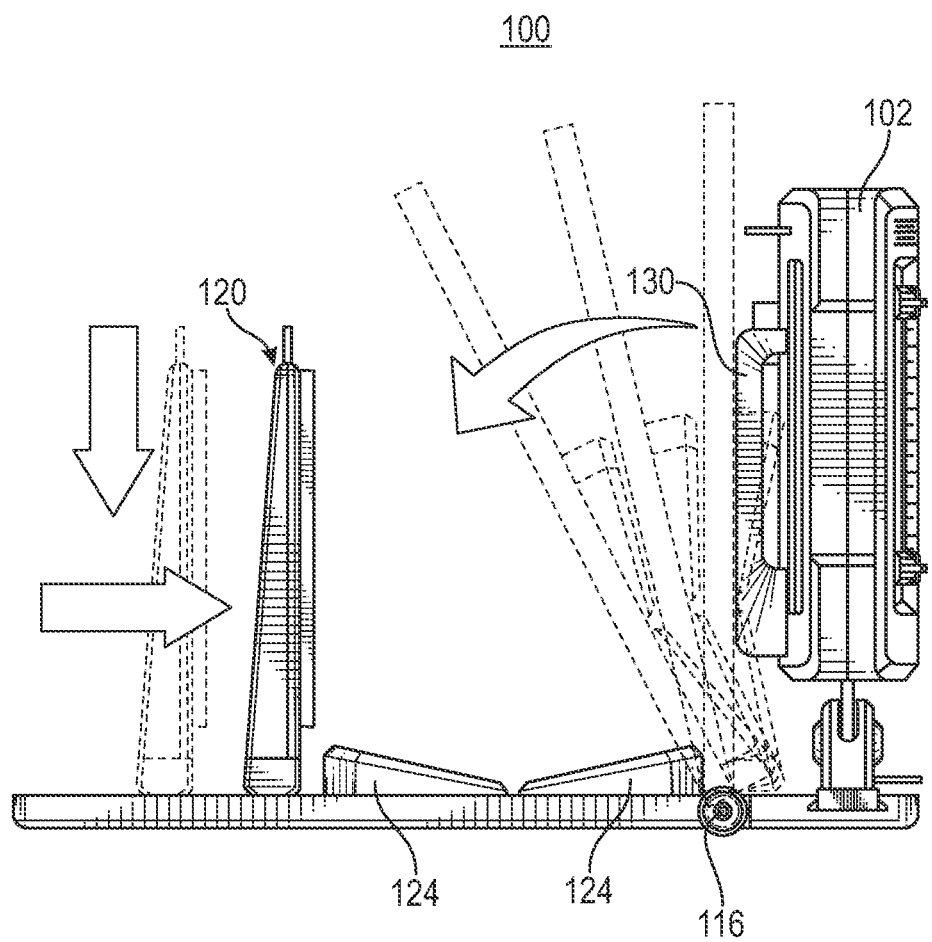

Referring to FIG. 3B, the portable headset 100 is unfolded by pulling the portion of the portable headset 100 (e.g., the second portion of the body) including the cushions 124 downward such that the second portion including the cushions 124 rotates downward about the pivot hinge 116. Accordingly, the second portion of the portable headset 100 including the cushions 124 rests atop the ground or floor. Then, the head restraint 120 is attached to the portion of the portable headset 100 including the cushions 124 at a location adjacent to the cushions 124. In some arrangements, the head restraint 120 is attached to the portion of the portable headset 100 including the cushions 124 by being slotted into the grooves 122 such that the head restraint 120 is capable of lateral movement along the grooves 122.

Figure 3C:
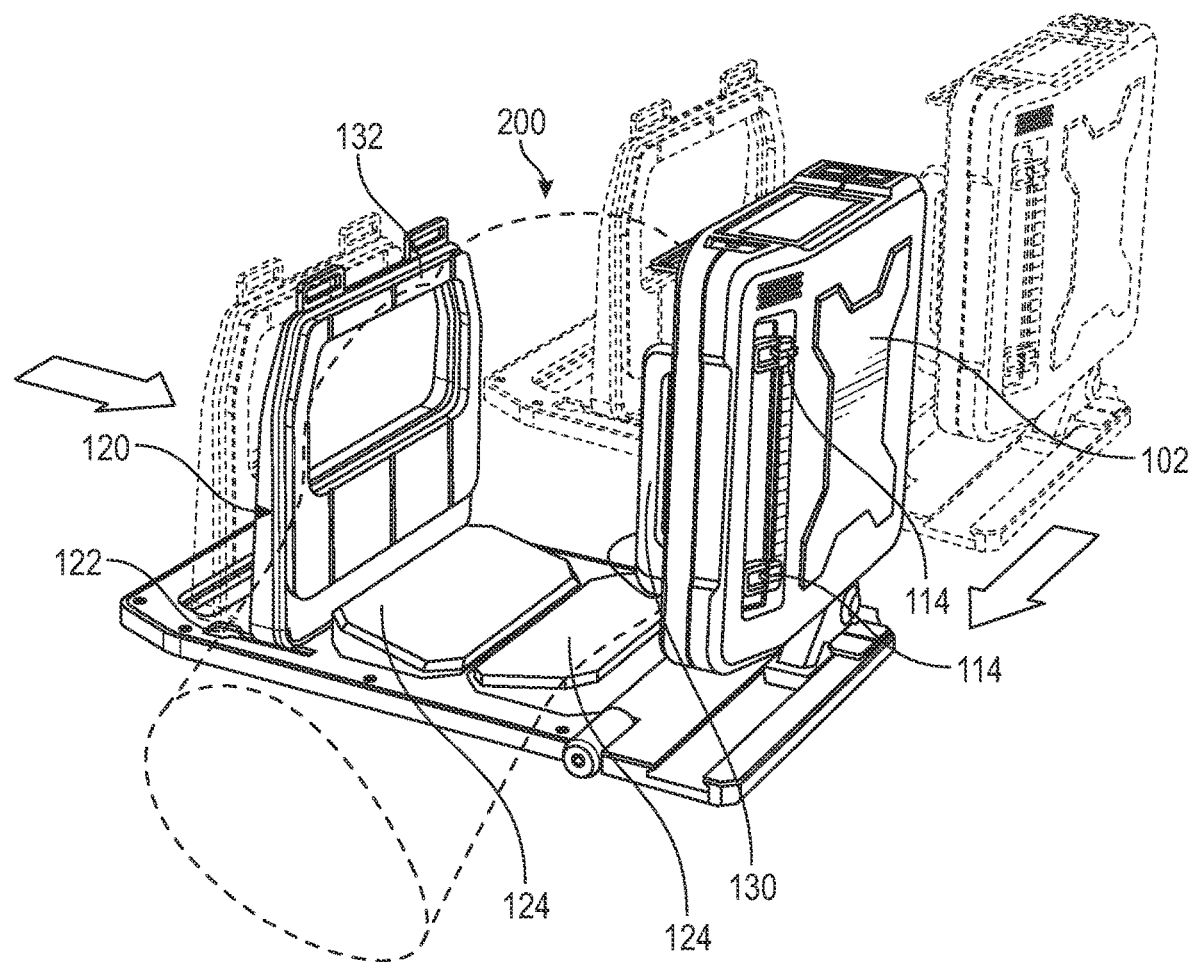

Referring to FIG. 3C, the portable headset 100 is shifted and positioned underneath the subject's head 200 such that the back of the subject's head 200 rests atop the cushions 124. Accordingly, the subject's head 200 is positioned between the head restraint 120 and the device 102. In some arrangements, the head restraint 120 is shifted towards the subject's head such that the padding 132 contacts the head 200 for restraining the head 200. In some arrangements, the head 200 contacts the guard 130 of the device 102. As such, in some arrangements, the subject's head 200 is restrained at both sides via the padding 132 of the head restraint 120 and via the guard 130 of the device 102.

Figure 3D:
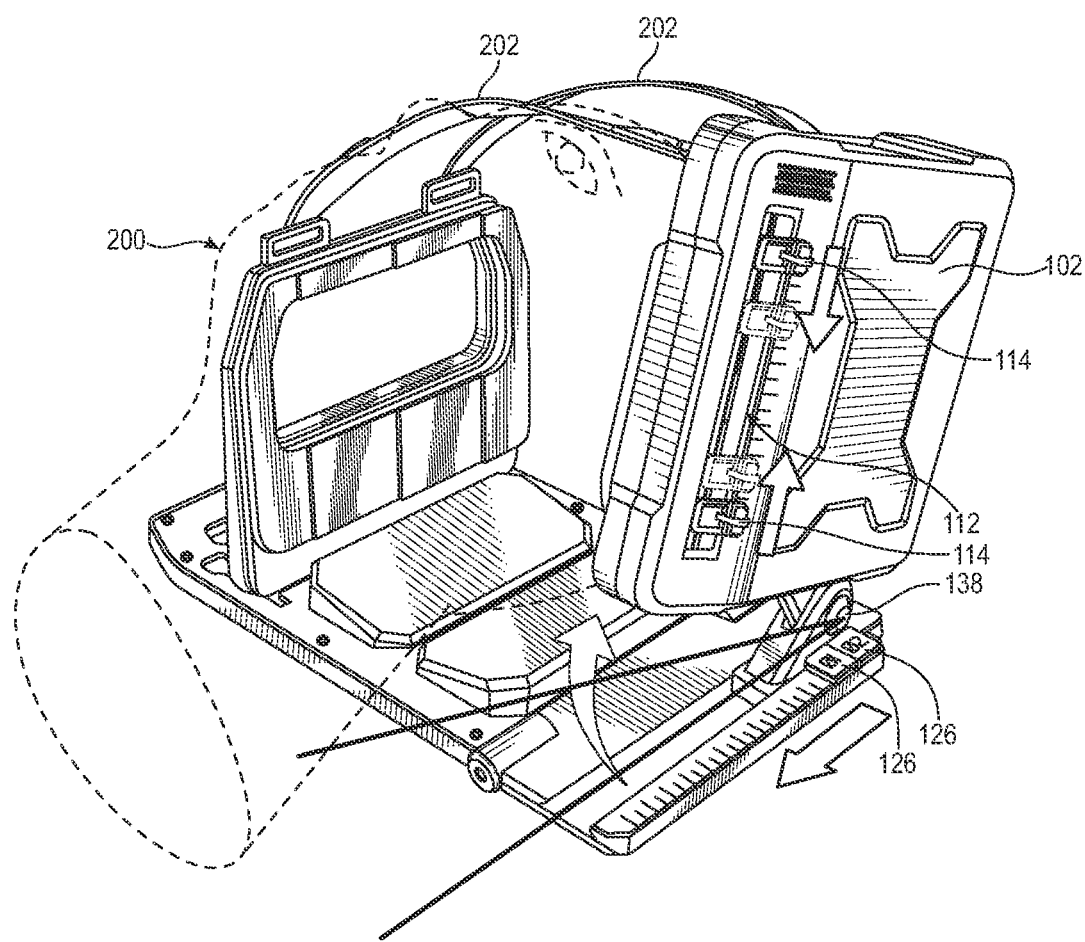

Referring to FIG. 3D, in particular arrangements, the straps 202 are fastened across the forehead of the subject's head 200, as described above. In some arrangements, the mechanical registration of the device 102 is performed once the head 200 is properly positioned and restrained within the portable headset 100. The mechanical registration includes pressing a first one of the tabs 126 to permit rotation of the device 102 about the tilt hinge 138. In some arrangements, an operator of the portable headset 100 tilts the device 102 at an appropriate position by monitoring the indicator (e.g., the line) that is within the registration window 112. For example, the operator tilts the device 102 such that the line within the registration window 112 is aligned along an imaginary line that connects the eye and the tragus of the subject's head 200. Such an orientation of the device 102 permits the device 102 to operate in the correct workspace along the subject's head 200. In other arrangements, the registration window 112 is appropriately aligned when positioned along other suitable facial features of the subject (e.g., along the temple and eye, along the cheekbone and tragus, and so on), as desired for permitting the effective operation of the device 102.

In some arrangements, once the registration window 112 is aligned along the appropriate facial features (e.g., along an imaginary line connecting the eye and the tragus of the subject's head 200), the registration markers 114 are moved along the registration window 112 such that each of the registration markers 114 overlaps an appropriate facial feature. For example, a first one of the registration markers 114 is moved to overlap an eye of the head 200 (e.g., an edge or corner of the eye) and a second one of the registration markers 114 is moved to overlap a tragus of the head 200. In other arrangements, the registration markers 114 are moved to overlap other suitable facial features of a subject (e.g., the temple and eye, the cheekbone and tragus, and so on), as desired for the effective operation of the device 102. In some arrangements, by positioning the registration markers 114 at particular features of the head 200, the boundaries of the workspace (e.g., scanning space) of the device 102 during its operation are defined. In other words, in some arrangements, the positioning of the registration markers 114 defines the boundaries of where the probe 136 can travel during operation of the device 102.

In some arrangements, the device 102 includes a linear encoder for converting the mechanical registration (e.g., a space between the registration markers 114, a space of the registration window 112, and the like), governed by the registration window 112 and the registration markers 114, into electrical signals for sending to the robotics of the device 102. In some arrangements, the electrical signals include directions regarding the boundaries of the workspace (e.g., as physically set by an operator of the portable headset 100 using the registration window 112 and the registration markers 114) to instruct the robotics of the device 102 on where the probe 136 should travel along the subject's head during operation.

Figure 3E:
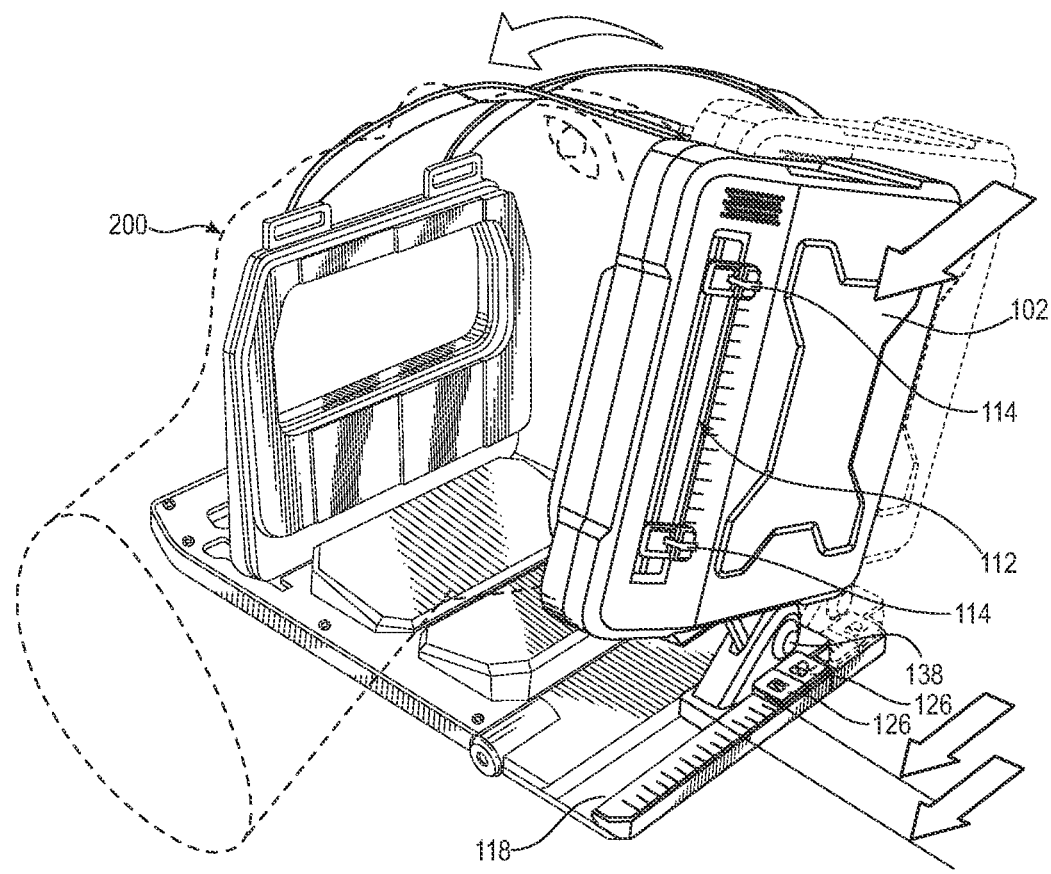

Referring to FIG. 3E, in some arrangements, after setting the appropriate orientation of the device 102, an operator presses the second one of the tabs 126 to permit lateral movement of the device 102 along the track 118. For example, because facial features of the subject's head 200 are used for registration of the device 102, the device 102 is shifted forward (e.g., towards the subject's chin) since the probe 136 is not completely within the appropriate workspace, as the portion of the device 102 including the registration window 112 and registration markers 114 occupies a portion of the workspace to be utilized by the device 102. As such, by shifting the device 102 forward, the probe 136 is then properly positioned to scan within the appropriate workspace. In some arrangements, after depressing the second one of the tabs 126, the device 102 is configured to shift forward a predetermined distance from its current position, for example, a distance in a range of about 0.5 inch to about 2.5 inches (e.g., about 1.25 inches). In other arrangements, the device 102 is configured to shift forward until reaching a predetermined marker location along the track 118 (e.g., the lateral movement of the device 102 is predefined with built-in mechanical stops). In some arrangements, the lateral movement of the device 102 is defined by a third registration marker that identifies a location of a feature of a subject (e.g., nose, forehead, temple, and so on).

Figure 3F:
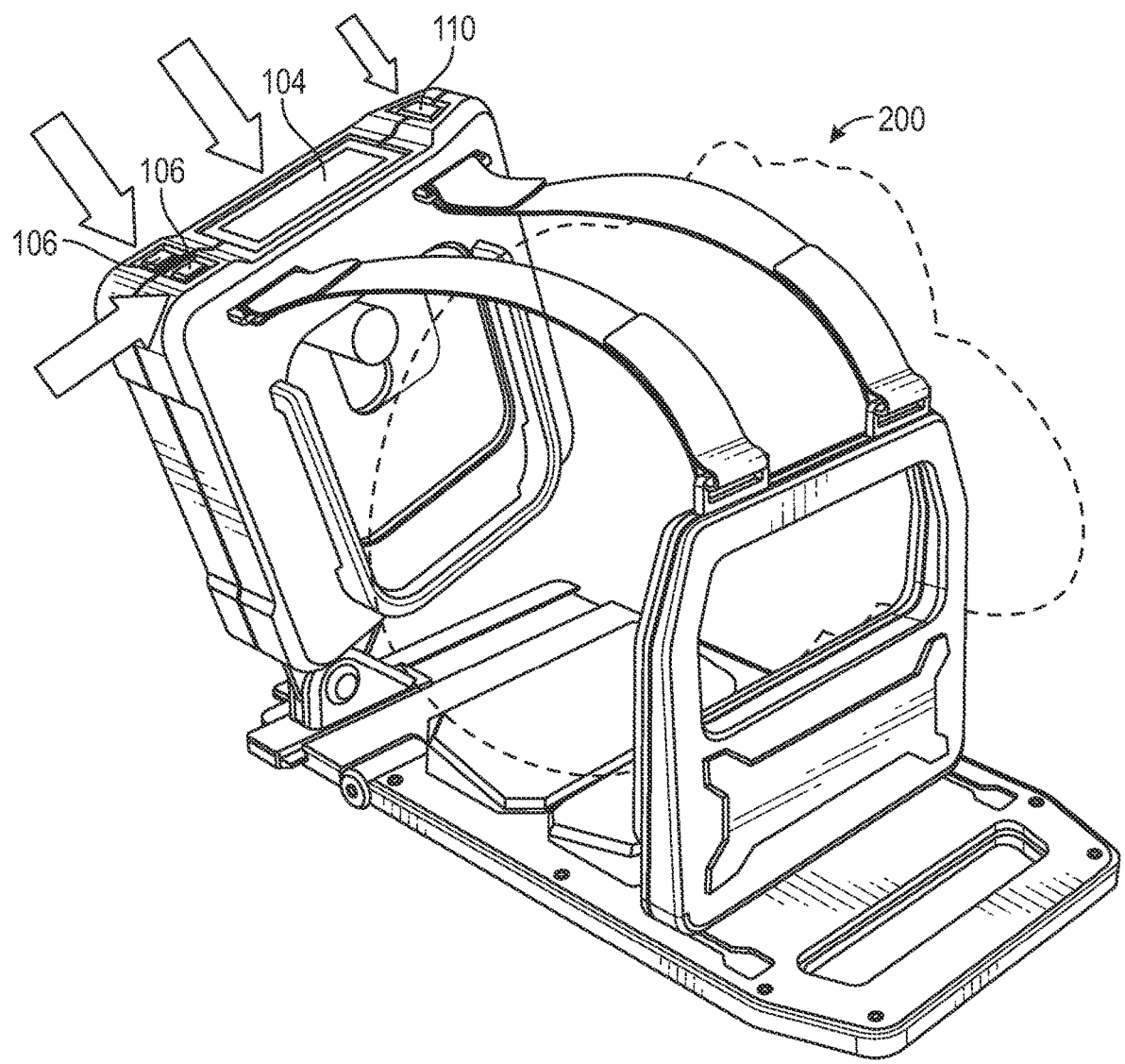

Referring to FIG. 3F, in some arrangements, inputs of the device 102 are actuated to provide instructions to the device 102. For example, an operator can turn on the device 102 using the power input 110. Furthermore, as an example, instructions to the device 102 (e.g., begin operation, cancel operation, display results, and so on) can be provided via interaction with the inputs 106, the display 104, the speaker 128, and the like.

Figure 4A:
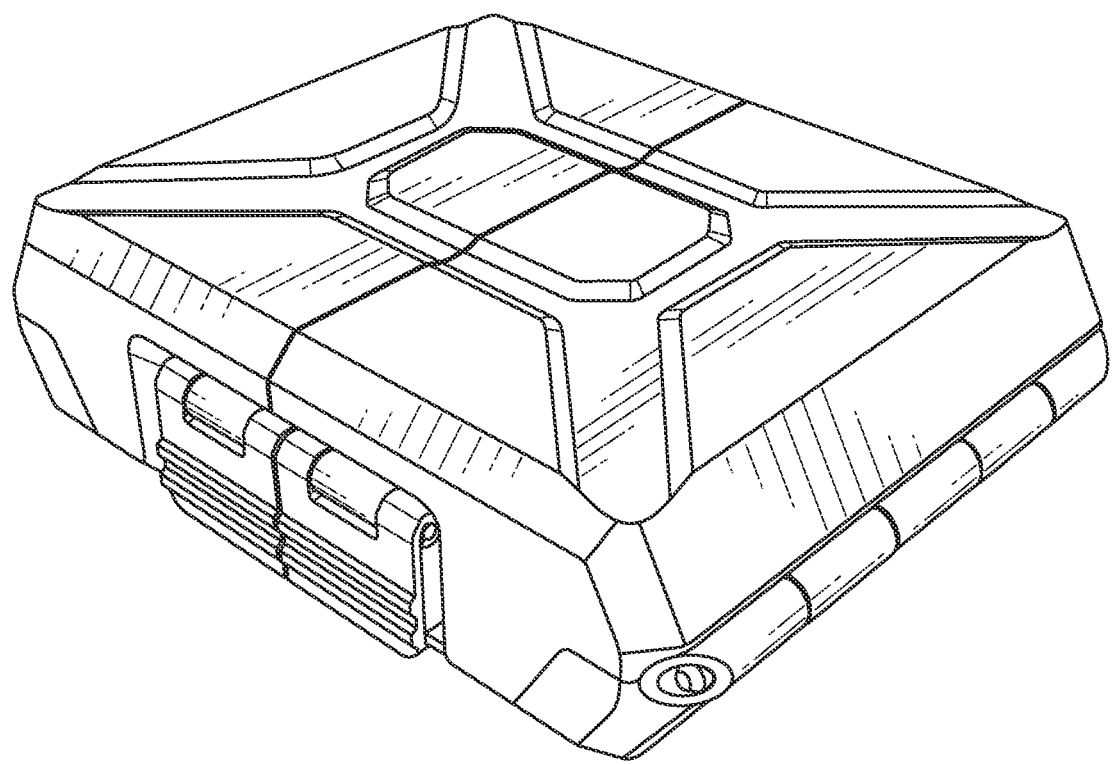
FIG. 4A and FIG. 4B illustrate a closed view and an open view, respectively, of a portable headset according to various arrangements.
Figure 4B:
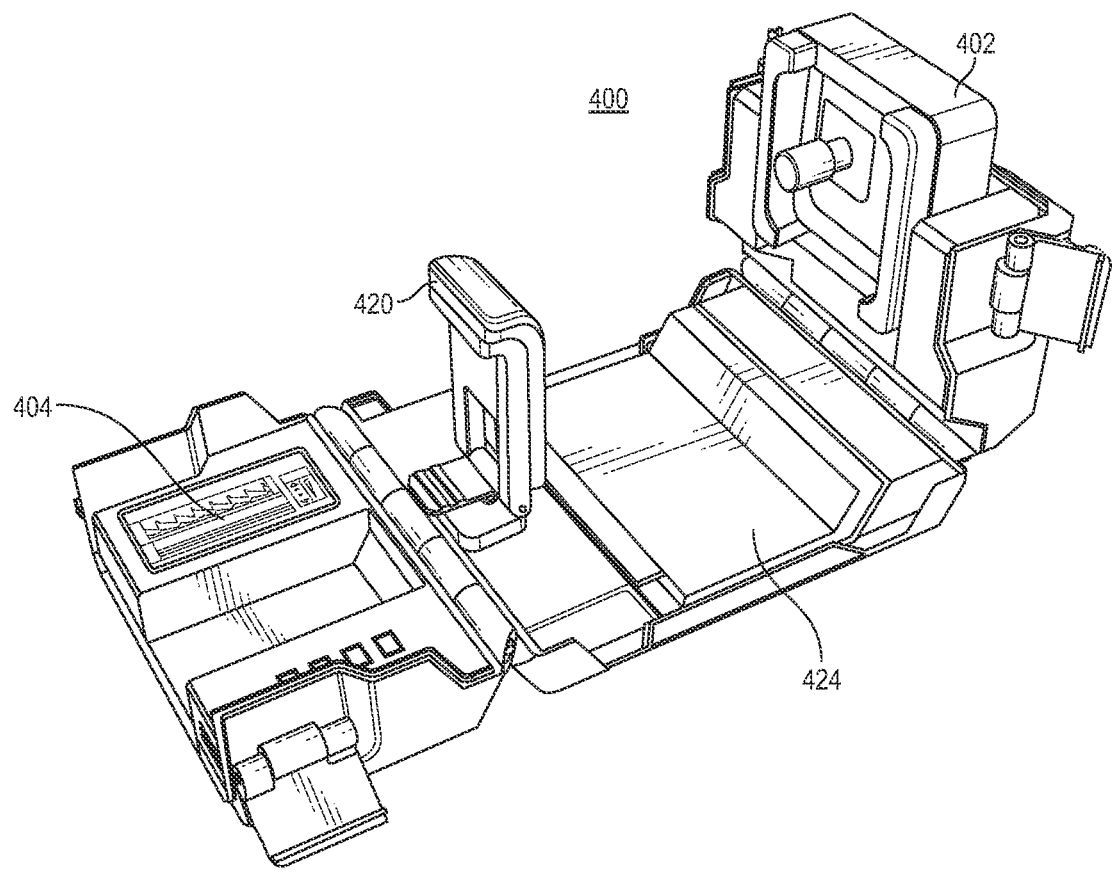

FIG. 4A and FIG. 4B illustrate a closed view and an open view, respectively, of a portable headset 400 according to various arrangements.

In some arrangements, the portable headset 400 is designed so as to be completely enclosed when in the folded or stored state. Accordingly, the components of the portable headset 400 are afforded increased protection from outside forces. In some arrangements, the portable headset 400 includes a device 402, a cushion 424, a head restraint 420, and a display 404. In particular arrangements, the device 402 is similar to the device 102 described above, the cushion 424 is similar to the cushion 124 described above, the head restraint 420 is similar to the head restraint 120 described above, and the display 404 is similar to the display 104 described above. Accordingly, the disclosure of the similar components described above is applicable to the device 402, the cushion 424, the head restraint 420, and the display 404, respectively. In some arrangements, one or more (or all) of the features described above with respect to the portable headset 100 can be implemented in the portable headset 400.

In some arrangements, the headsets described herein are used in conjunction with a bed (e.g., a gurney) such that the subject can lay down into the headsets so that the subject's head is horizontal (e.g., the subject is in a supine position). Accordingly, in some arrangements, the patient's head is not burdened with the weight of the headset, as the weight of the device mounted to the headset and the other components of the headset are supported by the platform on which the headset is placed (e.g., the ground). In some arrangements, a back side of the headset that contacts and lays on top of the ground is layered with a soft or pliable material (e.g., foam, an inflatable bladder, and the like) such that the soft layer conforms to the shape of the ground. For example, in some arrangements, the headset including the soft or pliable back surface that is conformable to the ground can be placed atop uneven (e.g., rocky) surfaces such that the device of the headset still performs effectively since the headset will not shift or sway due to the uneven ground.

In other arrangements, the headsets described herein are positioned such that a subject is in a seated position, and the subject's head is vertical. In particular arrangements, the headset is mounted on a vertical platform such that the subject's head bears little or no weight of the headset. For example, the vertical headset can be mounted on a wall, a chair, and the like.

The above used terms, including "held fast," "mount," "attached," "coupled," "affixed," "connected," "secured," and the like are used interchangeably. In addition, while certain arrangements have been described to include a first element as being "coupled" (or "attached," "connected," "fastened," etc.) to a second element, the first element may be directly coupled to the second element or may be indirectly coupled to the second element via a third element.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but are to be accorded the full scope consistent with the language, wherein reference to an element in the singular is not intended to mean "one and only one" unless specifically so stated, but rather "one or more." Unless specifically stated otherwise, the term "some" refers to one or more. All structural and functional equivalents to the elements of the various aspects described throughout the previous description that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

It is understood that the specific order or hierarchy of steps in the processes disclosed is an example of illustrative approaches. Based upon design preferences, it is understood that the specific order or hierarchy of steps in the processes may be rearranged while remaining within the scope of the previous description. The accompanying method claims present elements of the various steps in a sample order, and are not meant to be limited to the specific order or hierarchy presented.

The various examples illustrated and described are provided merely as examples to illustrate various features of the claims. However, features shown and described with respect to any given example are not necessarily limited to the associated example and may be used or combined with other examples that are shown and described. Further, the claims are not intended to be limited by any one example.

The foregoing method descriptions and the process flow diagrams are provided merely as illustrative examples and are not intended to require or imply that the steps of various examples must be performed in the order presented. As will be appreciated by one of skill in the art the order of steps in the foregoing examples may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The previous description of the disclosed implementations is provided to enable any person skilled in the art to make or use the disclosed subject matter. Various modifications to these implementations will be readily apparent to those skilled in the art, and the generic principles defined herein may be applied to other implementations without departing from the spirit or scope of the previous description. All structural and functional equivalents to the elements of the various aspects described throughout the previous description that are known or later come to be known to those of ordinary skill in the art are expressly incorporated herein by reference and are intended to be encompassed by the claims. Thus, the previous description is not intended to be limited to the implementations shown herein but is to be accorded the widest scope consistent with the principles and novel features disclosed herein.

What is claimed is:

1. A headset, comprising:
    a housing, containing:
        a transducer configured to collect data with respect to a subject, wherein the transducer is configured to transmit and receive ultrasound energy waves with respect to the subject; and
        a registration system configured to register the transducer with respect to the subject, the registration system comprising a registration window having at least one limit and one or more registration markers wherein the one or more registration markers are configured to be moved within the limit, the one or more registration markers configured to define a region of the object within which movement of the transducer is restricted based on an area bounded by the one or more registration markers, the transducer being configured to move along a first axis of movement within the area bounded by the one or more registration markers; and
    a housing pivot, comprising:
        a slide, configured to be disposed within a track of a base and configured to allow the housing to translate within the track along a second axis of movement; and
        a tilt hinge, coupled to the housing on a first end and to the slide on a second end, the tilt hinge configured to rotate the housing with respect to the slide to rotate the first axis relative to the second axis.

2. The headset of claim 1, comprising the one or more registration markers comprising a first registration marker located in the registration window, the first registration marker configured to move within the registration window.

3. The headset of claim 2, wherein a first position of the first registration marker defines the region of the object.

4. The headset of claim 2, comprising the one or more registration markers comprising a second registration marker located in the registration window, the second registration market configured to move within the registration window, wherein a first position of the first registration marker and a second position of the second registration marker define the region of the object.

5. The headset of claim 2, wherein the track allows for translation of the housing along a translation plane, wherein the rotation of the tilt hinge is within the translation plane, and wherein the tilt hinge is configured to rotate the second axis within the translation plane.

6. The headset of claim 1, further comprising:
a base, configured to receive the subject, wherein the base comprises the track.

7. The headset of claim 6, wherein the housing pivot further comprises:
a first tab, configured to allow rotation of the tilt hinge when pressed to rotate the first axis relative to the second axis; and
a second tab, configured to allow translation of the slide along the second axis when pressed.

8. The headset of claim 6, wherein the base further comprises:
a first portion, comprising the track;
a second portion; and
a pivot hinge, configured to allow the first portion to rotate relative to the second portion.

9. The headset of claim 8, wherein the wherein the pivot hinge is configured to rotate between a first orientation and a second orientation, the first portion and the second portion being colinear in the first orientation, and the first portion and the second portion being disposed at a 90 degree angle in the second orientation.

10. The headset of claim 6, wherein the base further comprises a pad.

11. The headset of claim 6, comprising a side element coupled to the base, wherein the side element and the housing face each other when the system is deployed, and the side element and the housing are connected via the base.

12. A system, comprising:
a transducer configured to collect data with respect to a subject, wherein the transducer is configured to transmit and receive ultrasound energy waves with respect to the subject;
a housing enclosing at least a portion of the transducer and configured to allow the transducer to translate along a first axis of movement;
a housing pivot, comprising:
a slide, configured to be disposed within a track of a base and configured to allow the housing to translate within the track along a second axis of movement; and
a tilt hinge, coupled to the housing on a first end and to the slide on a second end, the tilt hinge configured to rotate the housing with respect to the slide to rotate the first axis relative to the second axis; and
the base coupled to the housing pivot, the base configured to support the subject, wherein:
in a first state, the base and the housing are in a first arrangement; and
in a second state, the base and the housing are in a second arrangement, the first arrangement is different from the second arrangement.

13. The system of claim 12, comprising robotics configured to move the transducer, the housing enclosing the robotics.

14. The system of claim 12, wherein the housing comprises a registration window.

15. The system of claim 12, wherein the first arrangement comprises a first angle between the base and the housing, the second arrangement comprises a second angle between the base and the housing, the first angle being different from the second angle.

16. The system of claim 15, wherein the second angle is a 90 degree angle.

17. The system of claim 12, further comprising a pivot hinge configured to transition the system from the first state to the second state.

18. The system of claim 12, further comprising:
a side element coupled to the base, wherein the side element and the housing face each other in the first arrangement.

19. A system, comprising:
a transducer configured to collect data with respect to a subject, wherein the transducer is configured to transmit and receive ultrasound energy waves with respect to the subject;
robotics configured to move the transducer;
a registration window;
at least one registration marker;
a housing supporting the transducer, the robotics, the registration window, and the at least one registration marker, wherein a position of the at least one registration marker limits movement of the transducer along a first axis of movement as moved by the robotics;
a housing pivot, comprising:
a slide, configured to be disposed within a track of a base and configured to allow the housing to translate within the track along a second axis of movement; and
a tilt hinge, coupled to the housing on a first end and to the slide on a second end, the tilt hinge configured to rotate the housing with respect to the slide to rotate the first axis relative to the second axis; and
the base coupled to the housing pivot, the base configured to support the subject.

20. The system of claim 19, comprising a restraint, wherein a surface of the restraint faces a surface of the housing when the system is deployed.

* * * * *